United States Patent [19]

Fujii et al.

[11] Patent Number: 4,730,076

[45] Date of Patent: Mar. 8, 1988

[54] PROCESS FOR PRODUCING α-ASPARTYL-PHENYLALANINE ESTER

[75] Inventors: Tadashi Fujii, Iwatsuki; Hiroshi Yagiuchi; Akikazu Mitsunobu, both of Tokyo; Shigeru Aoki, Matsudo; Makoto Tsuda, Saitama, all of Japan

[73] Assignee: Nippon Kayaku Kabushiki Kaisha, Tokyo, Japan

[21] Appl. No.: 942,146

[22] Filed: Dec. 16, 1986

[30] Foreign Application Priority Data

Dec. 18, 1985 [JP] Japan .................. 60-283048
Jan. 14, 1986 [JP] Japan .................... 61-4251

[51] Int. Cl.[4] .......................... C07C 101/02
[52] U.S. Cl. ................................... 560/41
[58] Field of Search .............. 560/41; 530/801

[56] References Cited

U.S. PATENT DOCUMENTS

| 3,879,372 | 4/1975 | Boesten | 560/41 |
| 3,933,781 | 1/1976 | Bachman et al. | 560/41 |
| 4,021,418 | 5/1977 | Takemoto et al. | 560/171 |

FOREIGN PATENT DOCUMENTS

| 1187075 | 5/1985 | Canada | 560/41 |
| 0099855 | 2/1984 | European Pat. Off. | |
| 149263 | 7/1985 | European Pat. Off. | 560/41 |
| 48-812 | 1/1973 | Japan . | |
| 2609 | 6/1985 | PCT Int'l Appl. | 560/41 |

OTHER PUBLICATIONS

Geiger et al., *Chem. Ber.* 102, 2487-2490 (1969).

*Primary Examiner*—Michael L. Shippen
*Assistant Examiner*—Bruce D. Gray
*Attorney, Agent, or Firm*—Banner, Birch, McKie & Beckett

[57] ABSTRACT

The present invention relates to a process for producing α-aspartyl-phenylalanine ester represented by the general formula

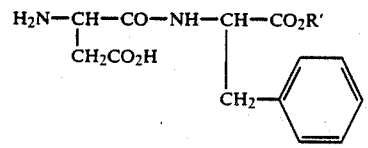

wherein R' represents an alkyl group having 1 to 4 carbon atoms, by reducing an N-protected-N-hydroxymethyl-α-aspartyl-phenylalanine ester represented by the general formula

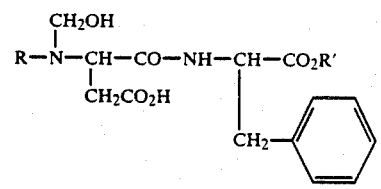

wherein R represents an organic mioety which can be substituted reductively by hydrogen, and R' is as defined above, with hydrogen gas or formic acid, in the presence of a reduction catalyst and an aromatic primary amine. According to the present invention, there can be obtained a high purity α-aspartyl-phenylalanine ester with a high yield.

11 Claims, No Drawings

PROCESS FOR PRODUCING α-ASPARTYL-PHENYLALANINE ESTER

BACKGROUND OF THE INVENTION

1. FIELD OF THE INVENTION

The present invention relates to α-aspartyl-phenylalanine ester represented by the general formula (I)

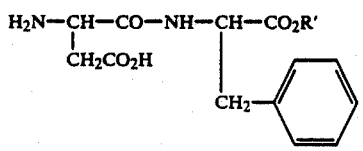

wherein R' represents an alkyl group having 1 to 4 carbon atoms.

α-Aspartyl-phenylalanine ester is useful as a low calorie sweetening agent, and have attracted public attention recently.

2. DESCRIPTION OF THE PRIOR ART

As a process for producing α-aspartyl-phenylalanine ester, there has already been proposed a process which comprises condensing α-[3-substituted-5-oxooxazolidinyl-(4)]acetic acid represented by the general formula (II)

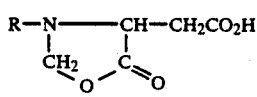

wherein R represents an organic moiety which can be substituted reductively by hydrogen, with phenylalanine alkyl ester represented by the general formula (III)

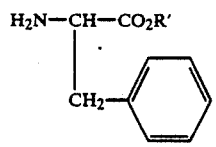

(wherein R' is as defined above) to obtain an N-protected-α-aspartyl-phenylalanine ester represented by the general formula (V)

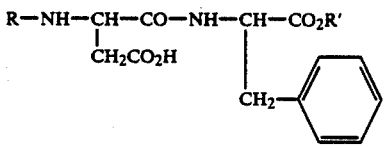

(wherein R and R' are as defined above) and reducing the compound (V) in a hydrogen atmosphere to obtain α-aspartyl-phenylalanine ester represented by the general formula (I) (Japanese Patent Publication No. 812/73). However, according to detailed study of the above-mentioned process made by the present inventors, it was found that the condensation of the compound (II) with the compound (III) does not give the compound (V), but give an N-protected-N-hydroxymethyl-α-aspartyl-phenylalanine ester represented by the general formula (IV) mentioned later, and that during reduction step, a hydroxymethyl group of the compound of general formula (IV) is reduced to form a methyl group to give N-methyl-α-aspartyl-phenylalanine methyl ester (hereinafter referred to as "N-methyl form") as by-product, so that the yield of the compound of the general formula (I) is low.

On the other hand, there has also been proposed a process for producing a compound of the general formula (I) which comprises reducing an N-protected-α-aspartyl-phenylalanine ester represented by the general formula (V)

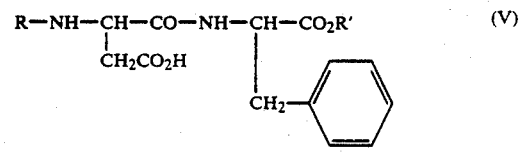

wherein R and R' are as defined above, with formic acid in the presence of a palladium catalyst (EP 99855).

SUMMARY OF THE INVENTION

According to the present invention, there is provided a process for producing α-aspartyl-phenylalanine ester represented by the general formula (I)

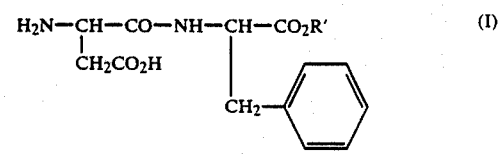

wherein R' is an alkyl group having 1 to 4 carbon atoms, by reducing an N-protected-N-hydroxymethyl-α-aspartyl-phenylalanine ester represented by the general formula (IV)

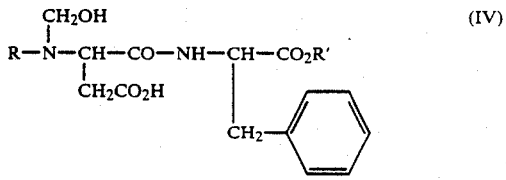

wherein R represents an organic moiety which can be substituted reductively by hydrogen, and R' is as defined above, with hydrogen gas or formic acid in the presence of a reduction catalyst and an aromatic primary amine.

According to the process of the present invention, there can be obtained a compound represented by the general formula (I) with high purity and high yield, because an N-protected group and N-hydroxymethyl group can be removed simultaneously without forming an N-methyl form as by-product.

DETAILED DESCRIPTION OF THE INVENTION

The present invention will be explained below in more detail.

As the R in the compound represented by the general formula (IV), any organic moiety may be used so long as they can be substituted by hydrogen reductively, among those used as a protective group of amino group in the peptide synthesis. For example, there may be illustrated substituted or unsubstituted benzyloxy carbonyl groups such as benzyloxycarbonyl group, alkoxybenzyloxycarbonyl groups (e.g., p-methoxybenzyloxycarbonyl group), halogenobenzyloxycarbonyl groups (e.g., p-chlorobenzyloxycarbonyl group), and nitrobenzyloxycarbonyl groups (e.g., p-nitrobenzyloxycarbonyl group). Among these, unsubstituted benzyloxycarbonyl group is preferred.

As the R' in the compound represented by the general formula (IV), there may be illustrated a lower alkyl group having 1 to 4 carbon atoms such as methyl, ethyl, propyl, and butyl groups.

As an asymmetric carbon in the compound represented by the general formula (IV), there may be L, D or DL.

Typical examples of the compound represented by the general formula (IV) include
N-Benzyloxycarbonyl-N-hydroxymethyl-α-aspartyl-phenylalanine methyl ester,
N-Benzyloxycarbonyl-N-hydroxymethyl-α-aspartyl-phenylalanine ethyl ester,
N-p-Methoxybenzyloxycarbonyl-N-hydroxymethyl-α-aspartyl-phenylalanine methyl ester,
N-p-Methoxybenzyloxycarbonyl-N-hydroxymethyl-α-aspartyl-phenylalanine ethyl ester,
N-p-Nitrobenzyloxycarbonyl-N-hydroxymethyl-α-aspartyl-phenylalanine methyl ester,
N-p-Nitrobenzyloxycarbonyl-N-hydroxymethyl-α-aspartyl-phenylalanine ethyl ester,
N-p-Chlorobenzyloxycarbonyl-N-hydroxymethyl-α-aspartyl-phenylalanine methyl ester and
N-p-Chlorobenzyloxycarbonyl-N-hydroxymethyl-α-aspartyl-phenylalanine ethyl ester.

Reduction reaction of the present invention can be carried out in a solvent in the presence of a reduction catalyst and an aromatic primary amine with hydrogen gas or formic acid under normal pressure or an elevated pressure.

As a solvent used in the present invention, any solvents may be used so long as they do not give any adverse effects to the reaction, and there may be illustrated lower alcohols such as methanol, ethanol, propanol, etc., ethers such as tetrahydrofuran, dioxane, etc., ketones such as acetone, methyl ethyl ketone, etc., esters such as methyl acetate, ethyl acetate, propyl acetate, etc., and mixed solvent of water and the above-mentioned organic solvent. Among these, a mixed solvent of water and methanol is specifically preferred. When formic acid is used, there may be also used as solvent water, N,N-dimethylformamide, dimethylsulfoxide, etc.

As a catalyst, there is no limitation so long as the catalyst can make reduction, but palladium type catalysts are preferred, and palladium-carbon as well as palladium black are specifically preferred. The amount of catalyst is 0.5% by weight or more to the compound represented by the general formula (IV), preferably 0.5 to 40% by weight, more preferably 1 to 15% by weight when hydrogen gas is used, and 5 to 30% by weight when formic acid is used.

As an aromatic primary amine used in the present invention, anilines which may be substituted by a lower alkyl group, a halogen atom, a nitro group or a lower alkoxy group are preferred. Concretely, there may be illustrated aniline, lower alkyl-substituted aniline such as o-toluidine, p-toluidine, etc., halogen-substituted aniline such as o-chloroaniline, m-chloroaniline, p-chloroaniline, etc., nitro-substituted aniline such as o-nitroaniline, m-nitroaniline, p-nitroaniline, etc., lower alkoxy aniline such as o-methoxyaniline, m-methoxyaniline, p-methoxyaniline, etc. Among them, aniline is preferred.

The amount of aromatic primary amine to be used is 0.1 to 3 equivalents, preferably 0.5 to 1.5 equivalents to the compound represented by the general formula (IV).

The amount of formic acid used in the present invention is 1 to 10 moles, preferably 1 to 3 moles per mole of the compound represented by the general formula (IV).

Reaction temperature depends on the solvent to be used, so that there is no special limitation thereto. However, it is generally within $-10°$ to $80°$ C., preferably $0°$ to $40°$ C. The reaction time is 0.5 to 3 hours.

α-Aspartyl-phenolalanine ester represented by the general formula (I) can be separated from the reaction solution by the following way:

The reaction solution is heated as it is or together with water to dissolve the product, a catalyst is removed by filtration from the solution, a solvent is concentrated under reduced pressure, and the residue is cooled to solidify it. Alternatively, pH of the reaction solution is adjusted to 1 to 2 with a hydrochloric acid solution to dissolve the product, a catalyst is removed by filtration, and then the filtrate is adjusted to pH of 4.5 to 5.5 with an aqueous ammonia to precipitate the product as crystal, which is then separated by filtration.

Next, an intended product obtained by Example 1 (mentioned later) and an intended product obtained by the known method (Japanese Patent publication No. 812/73, Example 3, reduction temperature=25 C.) are shown in Table 1 to compare the ratio of the intended product and the by-product (N-methyl form).

TABLE 1

| Method | Product | |
|---|---|---|
| | Intended product | By-product |
| Present invention | 100% | 0% |
| Known method | 50% | 50% |

As is apparent from Table 1, according to the known method, formation of by-product is very much, so that it is difficult to separate the intended product with a high purity. Thus, a purification step is absolutely necessary to obtain an intended product according to the known method. On the contrary, according to the present invention, there is produced no by-product, so that a high purity intended product can be obtained with a high yield, which is an excellent effect of the present invention.

The present invention will be explained below by way of Examples, but the invention is not restricted thereto.

EXAMPLE 1

Preparation of L-N-α-aspartyl-L-phenylalanine methyl ester

In 30 ml of a mixture of methanol and water (8:2), were dissolved 1.5 g (3.28 mmol) of L-N-benzyloxycarbonyl-N-hydroxymethyl-α-aspartyl-L-phenylalanine methyl ester and 0.24 g (2.62 mmol) of aniline. To the mixture, 0.15 g of 5%-palladium-carbon was added and hydrogen gas was passed therethrough for 2 hours while keeping the mixture at $0°$ to $5°$ C.

Then, the reaction mixture was heated to $45°$ to $50°$ C. to dissolve the crystal formed, a catalyst was removed by filtration, methanol was distilled off under reduced pressure to concentrate the filtrate until 15 ml, which was cooled to 5° to 0° C. to precipitate the product as crystal, which was then separated by filtration to give 0.95 g of the intended compound in the form of crystal (yield, 98.3%).

The resulting product had the same Rf value of TLC (Silica gel, developing solvent, n-butanol/acetic acid/water=4:1:1), IR, NMR, optical rotation and melting point as those of the standard sample separately synthesized.

EXAMPLE 2

Reaction was conducted in the same manner as in Example 1, except that the reduction with hydrogen gas was conducted at 20° to 25° C. in place of 0° to 5° C. to obtain 0.94 g of the intended compound (yield, 97.3%).

EXAMPLE 3

Preparation of L-N-α-aspartyl-L-phenylalanine methyl ester

L-N-benzyloxycarbonyl-N-hydroxymethyl-α-aspartyl-L-phenylalanine, methyl ester (1.5 g, 3.28 mmole) was dissolved in 17.6 ml of a mixture of methanol and water (10:1). Then, 0.61 g (13.12 mmol) of 98%-formic acid, 0.60 g (6.06 mmol) of aniline and 0.15 g of 5%-pallagium-carbon were added to the solution and the mixture was stirred for one hour at room temperature. The reaction solution was then adjusted to pH 2 to 2.5 with 6N-hydrochloric acid to dissolve crystals formed and then a catalyst was removed by filtration. To the filtrate, was added 28%-aqueous ammonia to adjust pH to 4.5 to 5.5, the filtrate was then stirred for one hour at 0° to 5° C. and subjected to filtration to give 1.11 g of the intended compound in the form of crystal (yield, 99.4%). The resulting crystal had the same Rf value of TLC (silicagel, developing solvent, n-butanol/acetic acid/water=4:1:1), IR, NMR, optical rotation and melting point as those of the standard sample separately synthesized.

EXAMPLE 4

Reaction was conducted in the same manner as in Example 3, except that 1.60 g (3.28 mmol) of L-N-p-methoxybenzyloxycarbonyl-N-hydroxymethyl-α-aspartyl-phenylalanin methyl ester was used in place of L-N-benzyloxycarbonyl-N-hydroxymethyl-α-aspartyl-L-phenylalamine methyl ester. There was obtained 0.92 g of the intended compound (yield, 82.4%).

REFERENCE EXAMPLE

Preparation of L-N-Benzyloxycarbonyl-N-hydroxymethyl-α-aspartyl-L-phenylalanine methyl ester To 55 ml benzene solution containing 8.08 g (80 mmol) of triethylamine, were added 5.58 g (20 mmol) of α-[3-benzyloxycarbonyl-5-oxooxazolidinyl-(4)]-acetic acid and 12.93 g (60 mmol) of phenylalanine methyl ester hydrochloride and dissolved. The resulting solution was stirred for 6 hours at 45° C. The reaction solution was admixed with 60 ml of benzene and extracted twice with 60 ml of water. The aqueous layers were combined, adjusted with 10%-hydrochloric acid to pH of 2 and then extracted twice with 80 ml of ethyl acetate. The ethyl acetate layers were combined, washed with once 40 ml of 1% hydrochloric acid, thrice with 70 ml of 10% saline water, and then the organic layer was dried over anhydrous magnesium sulfate and evaporated under reduced pressure to obtain 8.93 g of the intended compound (yield, 97.5%).

What is claimed is:

1. A process for producing α-aspartyl-phenylalanine ester represented by the general formula (I)

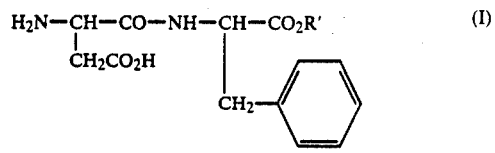

wherein R' represents an alkyl group having 1 to 4 carbon atoms, which comprises reducing an N-protected-N-hydroxymethyl-α-aspartyl-phenylalanine ester represented by the general formula (IV)

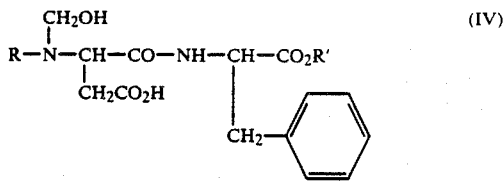

wherein R represents an organic moiety which can be substituted by hydrogen reductively, and R' is as defined above, with hydrogen gas or formic acid in the presence of a reduction catalyst and an aromatic primary amine.

2. A process according to claim 1, wherein R represents an unsubstituted benzyloxycarbonyl group or a benzyloxycarbonyl group substituted by a halogen atom, a lower alkoxy group, a lower alkyl group or a nitro group, R' represents a methyl group, a reduction catalyst represents a palladium type catalyst, and an aromatic primary amine represents an aniline which may be substituted by a lower alkyl group, a halogen atom, a nitro group or a lower alkoxy group.

3. A process according to claim 2, wherein R represents unsubstituted benzyloxycarbonyl group.

4. A process according to claim 1, wherein an amount of reduction catalyst is 0.5 to 40% by weight of the compound represented by the general formula (IV).

5. A process according to claim 1, wherein an amount of reduction catalyst is 1 to 15% by weight of the compound represented by the general formula (IV), when hydrogen gas is used, and is 5 to 30% by weight, when formic acid is used.

6. A process according to claim 1, wherein the aromatic primary amine is aniline.

7. A process according to claim 1, wherein an amount of the aromatic primary amine is 0.1 to 3 equivalents of the compound represented by the general formula (IV).

8. A process according to claim 1, wherein an amount of formic acid is 1 to 10 times by mol the compound represented by the general formula (IV).

9. A process according to claim 1, wherein the amount of aromatic primary amine is 0.5 to 1.5 equivalents and the amount of formic acid is 1 to 3 times by mol to the compound represented by the general formula (IV).

10. A process for producing α-aspartyl-phenylalanine lower alkyl ester which comprises reducing N-benzyloxycarbonyl-N-hydroxymethyl-α-aspartyl-phenylalanine lower alkyl ester with hydrogen gas in a mixed solvent of water and a lower alcohol in the presence of palladium-carbon and aniline.

11. A process for producing α-aspartyl-phenylalanine lower alkyl ester which comprises reducing N-benzyloxycarbonyl-N-hydroxymethyl-α-aspartyl-phenylalanine lower alkyl ester with formic acid in a mixed solvent of water and a lower alcohol in the presence of palladium-carbon and aniline.

* * * * *